(12) United States Patent
Barathur et al.

(10) Patent No.: US 8,404,745 B2
(45) Date of Patent: *Mar. 26, 2013

(54) TRANSDERMAL DELIVERY OF MEDICINAL CETYLATED FATTY ESTERS USING PHONOPHORESIS OR IONTOPHORESIS

(76) Inventors: Raj R. Barathur, Escondido, CA (US); Jack B. Bookout, San Diego, CA (US)

( * ) Notice: Subject to any disclaimer, the term of this patent is extended or adjusted under 35 U.S.C. 154(b) by 260 days.

This patent is subject to a terminal disclaimer.

(21) Appl. No.: 13/049,557

(22) Filed: Mar. 16, 2011

(65) Prior Publication Data

US 2012/0265119 A1    Oct. 18, 2012

(51) Int. Cl.
*A61K 31/23*    (2006.01)
(52) U.S. Cl. .................................................. 514/552
(58) Field of Classification Search ................... 514/552
See application file for complete search history.

(56) References Cited

U.S. PATENT DOCUMENTS

2003/0153620 A1* 8/2003 Meakin et al. ............... 514/552

* cited by examiner

*Primary Examiner* — Blessing Fubara
*Assistant Examiner* — Jennifer Berrios

(57) ABSTRACT

The use of phonophoresis or iontophoresis to enhance transdermal delivery of medicinal Cetylated fatty esters when applied in cream or gel compositions is disclosed. These compositions provide hydrophilic salt forms and penetration-enhancing vehicles that work in conjunction with phonophoresis or iontophoresis to increase the efficacy of the medicinal actives.

10 Claims, 1 Drawing Sheet

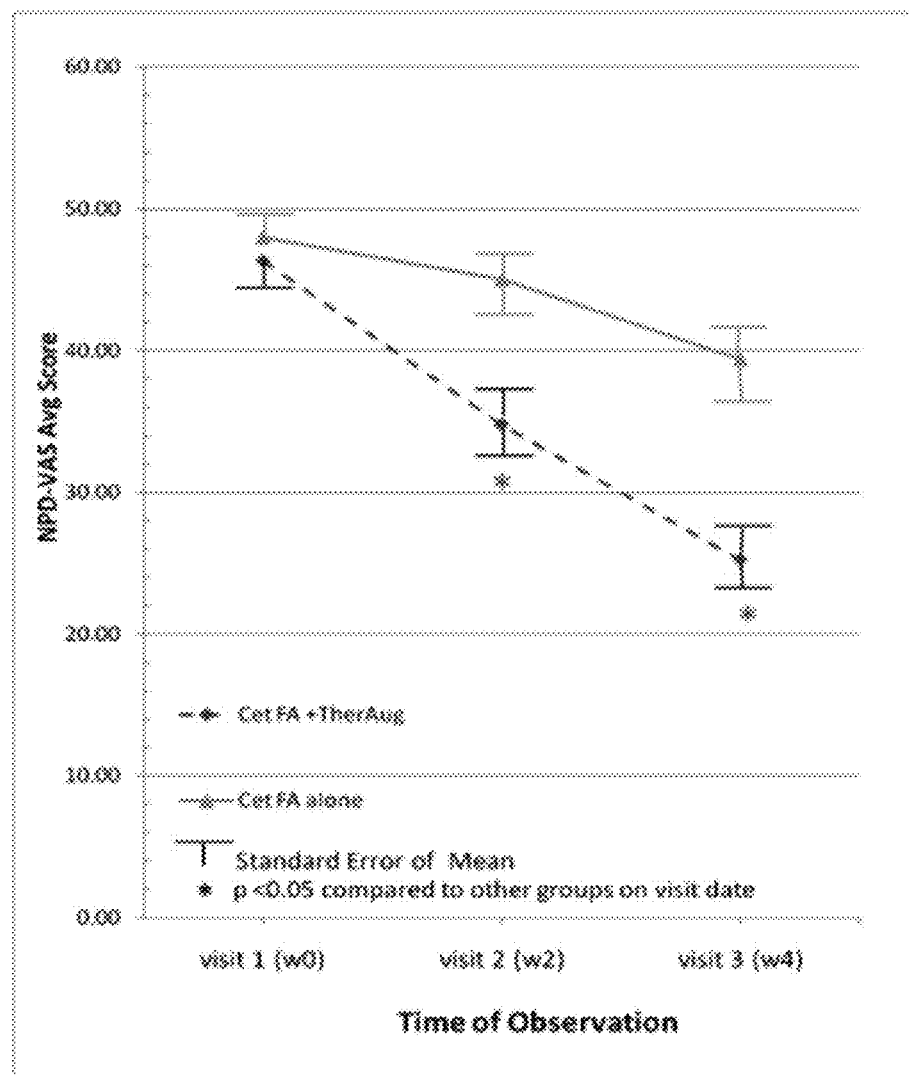
Treatment Responses as Measured by NPD-Pain VAS Scores.

TRANSDERMAL DELIVERY OF MEDICINAL CETYLATED FATTY ESTERS USING PHONOPHORESIS OR IONTOPHORESIS

CROSS-REFERENCE TO RELATED APPLICATIONS

Not applicable

STATEMENT REGARDING FEDERALLY SPONSORED RESEARCH OR DEVELOPMENT

Not applicable

TECHNICAL FIELD

The present invention relates to compositions of creams, lotions and gels designed specifically to enhance delivery of medicinal Cetylated fatty esters when either phonophoretic or iontophoretic techniques are utilized to facilitate the transdermal delivery of the medicament.

BACKGROUND OF INVENTION

The Applications of Cetylated Fatty Esters in Pain Management.

The medicinal utilization of Cetylated fatty acids were first described in U.S. Pat. No. 4,049,824, Diehl, issued Sep. 20, 1977 and U.S. Pat. No. 4,113,881, Diehl, issued Sep. 12, 1978. These patents provide examples for the oral utilization of cetyl myristoleate in effective amounts for the treatment of inflammatory rheumatoid arthritis in mammals. In U.S. Pat. No. 5,569,676, Diehl, issued Oct. 29, 1996 extended treatment claims for cetyl myristoleate to treat osteoarthrits and to include topical and parenteral modes of delivery. U.S. Pat. No. 6,417,227, Lord and Lytle, issued July, 2002 describes the use of cetyl myristoleate in the oral treatment of tendinitis, tenosynovitis, bursitis, chronic patellar tendinitis, Achilles tendinitis, fibrositis, inflammation of spine, colitis, bronchitis, polymyalagia rheumatic, Crohn's disease, primary biliary cirrhosis, pericarditis, ulcerative colitis and Sjogren's syndrome. Cetyl myristoleate, as described in this patent, when administered in a dissolution resistant-coated capsule was noted to have therapeutic properties which could be applied to multiple condition types having associated inflammation and immune mediated pain. U.S. Pat. No. 6,677,321, Levin, issued Jan. 13, 2004 extended the oral administration of cetyl myristoleate for treating inflammatory diseases, when the cetyl myristoleate or one or more esters of unsaturated fatty acids and fatty alcohols are used in conjunction with at least one tetracycline compound, an NSAID, a COX-2 inhibitor, a corticosteroid, S-adenylmethionine or a synovial fluid supplement. For purposes of this disclosure, the Cetylated fatty esters are defined as a select group of fatty acids that have been converted synthetically into cetyl esters, some with saturated and some unsaturated hydrocarbon chains, but with the number of carbon atoms of these chains ranging from 10 to 18 or more in length. The composition of these select groupings often includes but is not limited to the inclusion of cetyl myristoleate.

The utilization of topical or oral applications of a selected group of Cetylated fatty esters has been described for treatment of periodontal disease in U.S. Pat. No. 7,612,111, Spencer and Millsap, issued Nov. 3, 2009 and U.S. Pat. No. 7,776,914, Spencer and Millsap, issued Aug. 17, 2010. These patents also incorporate lecithin, olive oil and mixed tocopherols as part of their treatment compositions. U.S. Pat. No. 7,772,279, Leonard and Simonton, issued Aug. 10, 2010 discloses the oral use of a vegetable-derived, vegetable butter-based cetyl myristoleate for treatment of musculoskeletal inflammation in animals, especially equines.

These patents are supported by numerous publications that define medicinal properties of the cetyl fatty esters. Research has shown that certain Cetylated fatty esters act to relieve pain, improve joint mobility and return physical function due to affected joints in humans and in animal models. Other non-arthritic conditions that include myofascial pain syndrome and sports-related pain injuries have also demonstrated therapeutic potential. For reference in defense of these claims the following are added herein: Hesslink et al., J Rheumatol, 29, pp. 1708-1812 (2002); Kraemer et al., J Rheumatol, 31, pp. 767-774 (2004); Kraemer et al., J Strength Condit Res 19, pp. 475-480; Kraemer et al., J Strength Condit Res 19, pp. 115-121 (2005); Siemandi, Townsend Lett Doctors & Patients, August/September, pp 58-63 (1997); Sharan et al., Manual Therapy, 14 (supp), pp. S1-53 (2009); Edwards, J Nutr Environ Med, pp. 105-111 (2007); Hunter et al., Pharm Res, 47, pp. 43-47 (2003).

It is clear that the therapeutic utilization of Cetylated fatty esters has a history of at least two decades. The efficacy of these medicinal actives is associated with the need of multiple dosing applications in order to get sufficient levels of absorption to obtain therapeutic results. Oral absorption can be facilitated in capsule powders through fine granulation and selected carrier excipients or in soft gel capsules through the use of lipophilic oil carriers. The use of lecithin, olive oils and other lipophilic compounds, for example, have been described in the patent discussions of oral Cetylated fatty ester treatment, noted above. The delivery of Cetylated fatty esters enter the skin and sub epidermal layers, allowing them to be used widely in topical formulations. The primary objective of this invention, however, was to possibly enhance the penetration of Cetylated fatty esters to greater concentrations using the disclosed gel, cream or lotion formulations in conjunction with phonophoresis or iontophoresis.

Transdermal Penetration Enhancement

Penetrant agents with lipophilic properties have been utilized for many years to enhance absorption of lipophilic drugs and are well known. Drug delivery through the skin barrier is restricted primarily to passive diffusion in accordance to Fick's law (solute diffusivity is inversely related to molecular size), due to the absence of active transport.

Fick's Law of Diffusion as it applies to drug transport across the stratum corneum can be stated as:

$$J_{ss} = \left(\frac{D \cdot K_{sc/veh}}{h}\right) \cdot C_{veh} = K_p \cdot C_{veh}$$

where $J_{ss}$ is the steady-state flux across stratum corneum (mg $cm^{-2}\ hr^{-1}$)

D is the diffusion coefficient or diffusivity of drug molecules ($cm^{-2}\ hr^{-1}$)

$C_{veh}$ is the drug concentration gradient across the stratum corneum (mg $cm^{-3}$)

$K_{sc/veh}$ is the partition coefficient of the drug between skin and formulation medium, K p is the formulation dependent permeability coefficient of the drug, and h is the thickness of the stratum corneum (Drug lipophilicity has a major effect on $K_{sc/veh}$ and many approaches to enhance drug delivery attempt to manipulate $K_{sc/veh}$ and $C_{veh}$).

Numerous drug delivery formulations have been developed to enhance diffusion or to increase skin permeability or to both enhance diffusion and increase permeability. It is well known through bioavailability comparisons of oral versus topical delivery of medicinal actives, the topical delivery generally may provide systemic concentrations of 2-10% that of oral delivery.

The literature abounds with formulations designed to facilitate transdermal delivery of various pharmaceutical actives. For a discussion of use of penetration enhancers in topical formulations the following citations are all hereby incorporated by reference: PERCUTANEOUS PENETRATION ENHANCERS (Eric W. Smith & Howard I. Maibach eds. 1995); Ghosh, T. K. et al., Pharmaceutical Technology, 17, p. 62 (1993); Ghosh, T. K. et al. Pharmaceutical Technology, 17, p. 68 (1993); Ghosh, T. K. et al. Pharmaceutical Technology, 17, p. 72 (1993).

U.S. Pat. No. 4,537,776, Cooper, issued Aug. 27, 1985, describes a means by which pharmaceutically-active agents can be delivered transdermally in greater concentrations through the use of N-(2-hydroxyethyl)pyrrolidone and a "cell-envelope disordering compound" as penetrating agents. The enhancement potential through topical use of penetrating agents with pharmaceutical actives is described U.S. Pat. No. 3,989,816, Rhaadhyaksha (using 1-substituted azacycloheptan-2-one with multiple types of actives), U.S. Pat. No. 4,132,781, Stoughton (using 2-pyrrolidone or an n-lower alkyl-2-pyrrolidone with antibiotics as actives), U.S. Pat. No. 4,017,641, DiGiulio (using 2-pyrrolidone and 2.5% propylene glycol in skin conditioning compositions), U.S. Pat. No. 4,343,709, Fawzi (using C5-C12 carbon length fatty acids with corticosteroid actives), and U.S. Pat. No. 3,934,013, Poulsen (using propylene glycol, fatty alcohol and water with at least two corticosteroids in the composition; the fatty alcohol being from 16-24 carbon atoms, preferably a saturated, monohydric primary alcohol such as cetyl alcohol, stearyl alcohol or behenyl alcohol). These are given for example, all of which are incorporated herein for reference.

A variety of lipophilic agent materials are described in European Patent No. 43,738, Wickett et al., published Jan. 13, 1982. In addition, different types of surfactants (lipophilic and hydrophilic), in combinations with hydrophilic co-solvents may also enhance bioavailability depending on the physical properties of the drug of interest. Co-solvent examples would be propylene glycol and ethanol. Examples of anionic surfactants include sodium lauryl sulfate (SLS); example of cationic surfactants encompass cetyltrimethyl ammonium bromide; nonionic surfactants and zwitterionic surfactant examples would include dodecyl betaine. U.S. Pat. No. 5,026,556, Drust et al, issued Jun. 25, 1991 describes the use of specific polar solvents (C3-C4 diols, C3-C6 triols and mixtures thereof) and polar lipid material (C8-C12 fatty alcohol or fatty acid esters) for enhanced transdermal delivery of buprenorphine. U.S. Pat. No. 4,864,970, Patel and Chang, issued Sep. 5, 1989 describes different formulation compositions specific for various medicinal actives which incorporate oleic acid, oleyl alcohol, glycerol monoleate, glycerol dioleate, glycerol trioleate (and mixtures thereof) with inert diluents (water, propylene or polypropylene glycols and mineral oil being exemplary). It is evident from these and other examples that combinations, which make up delivery systems, must be developed specifically for the actives being administered in order to optimize sufficient flux of active through the skin, while also minimizing side effects such as skin irritation. In general, increased tissue wetness promotes transdermal delivery of both hydrophilic and lipophilic permeants.

Mechanical Enhancement of Transdermal Delivery of Pharmaceutical Drugs

However, regardless of the multiplicity of penetration enhancing formulations specifically designed to facilitate drug transdermal delivery, mechanical methods of enhancing transdermal drug delivery, in general, have been found to be superior to these passive methods of delivery. These properties have been found to be overcome to the addition of the mechanical acceleration effects of ultrasound and iontophoresis, and these methods have the greatest interest for this disclosure. Other mechanical methods of enhancement and delivery of pharmaceutical drugs transdermally include: physical therapy (e.g., massage), electroporation, transdermal patches, implantable release devices/microchips, microneedle injection arrays, needleless injection devices, chemical or physical skin peels (microdermabrasion), magnetophoresis, and laser-radiation photomechanical wave devices. These other methods may form a basis for further disclosure at some other time.

Phonophoresis (Sonophoresis)

For this disclosure, phonophoresis is the use of ultrasound (US) to enhance permeation for a topically applied therapeutic agent, when either applied simultaneously with therapeutic agent or with US as a pretreatment step. It is closely associated with ultrasound physiotherapy, which is used in the treatment of soft-tissue injuries (such as tendinitis, tenosynovitis, epicondylitis, bursitis and osteoarthritis) but, in which topical application of a pharmaceutical drug is not being administered using ultrasound enhancement. Phonophoresis has been in practice since 1954 when this method was therapeutically demonstrated with hydrocortisone topical administration. Alternating electrical current applied to a transducer with a piezoelectric crystal is used to produce the sonic waves. Treatment duration, intensity and frequency of ultrasound utilization are key parameters that affect percutaneous absorption, the latter having the greatest effect. While frequencies between 20 kHz and 16 MHz have been documented as enhancing skin permeation, frequencies at the lower end of this range (<100 kHz) have been reported to provide the greatest effect on transdermal drug delivery. Through this approach macromolecules of molecular weight up to 48 kDa have been shown to be delivered through transcutaneous absorption. Diffusion of the topically applied drug can be enhanced by both the thermal and non-thermal properties of the ultrasonic sound waves. For example, heating can help dilate points of entry (e.g., hair follicles and sweat glands), increase peripheral circulation in the applied area and provide greater kinetic energy of the drug molecules being delivered. Both thermal and nonthermal effects can increase cell permeability. Reported improvements in transport efficiency range from 2-5000 fold depending on molecular properties of the drug.

A coupling media, usually a gel or cream that has conductive properties, is used to eliminate the air layer space and thus increase the delivery of ultrasonic energy to the skin and tissue. The composition of the coupling media is of high importance since ultrasound waves encountering a medium of dissimilar properties undergo refraction, reflection or absorption, or all three properties. As examples for reference of the synergistic interactions between chemical enhancers within coupling medias and iontophoresis, ultrasound and electroporation, the review by Mitragotri, Pharm. Research, 17, pp. 1354-1359 (2000) is herein incorporated, as well as the following citations: Choi et al., Appl. Skin Physiol., 12, pp. 326-335 (1999); Le et al., Pharm. Res., 17, 1151-1154 (2000); U.S. Pat. No. 5,947,921, Johnson et al., issued Sep. 7, 1999; and U.S. Pat. No. 5,115,805, Bommannan et al., issued May 26, 1993. U.S. Pat. No. 5,115,805 also discloses that the rates of drug permeation through the skin is enhanced by using specific frequencies of US. Frequencies greater than 10 MHz were cited as providing enhanced penetration.

Iontotophoresis

For this disclosure, iontophoresis (IS) is defined to be the method of enhancing permeation for a topically applied therapeutic agent through the application either directly or indirectly of a low level electric current. The amount of direct current is usually small (currently set limit of 0.5 mA/cm$^2$) and is applied through a drug containing electrode in skin contact and with a grounding electrode elsewhere on the body for circuit completion. Alternatively, two electrode chambers, one containing the drug, can be placed side by side on the skin. Enhancement mechanisms for iontophoresis are proposed to be one or more combination of electroosmosis, electropertubation and electrorepulsion. Effective delivery of drugs is dependent of several parameters: electrode type, current intensity, pH of system, competitive ion effect and the types of permeants in the coupling media.

Bhatia et al., Journal of Controlled Release, 47, pp. 81-89 (1997) describe the use of enhancers (penetrant agents as 10% oleic acid in combination with ethanol or with propylene glycol) as important in order to significantly enhance transdermal delivery of the active agent (luteinizing hormone releasing hormone). Clancy et al., International Journal of Pharmaceutics, 105, pp. 47-56 (1994) is also which are incorporated herein for reference of the avidity of enhancers in increasing iontophoresis efficacy. As a review of mechanical delivery methods, including iontophoresis and ultrasound, Brown et al., Meth. Molec. Biol., 437, pp. 119-139 (2008) is incorporated herein as a reference.

Polar molecules (with drugs having net negative charge being generally favored) are often shown to receive the greatest transdermal transport enhancement by this method. Highly lipophilic drugs, however, being more polar neutral may show less enhancement through iontophoresis usage. Absorption is shown to decline linearly as alkyl chain length increases. However, Gangarosa et al. Journal of Pharmacology and Experimental Therapeutics, 212, pp. 377-381 (1980) have described enhanced nonionic molecule transport due to the hydration of the stratum corneum with associated sodium ion transfer (iontohydrokinesis; a mass transport effect into the skin involving ions and water molecules). ELECTRICALLY ASSISTED TRANSDERMAL AND TOPICAL DRUG DELIVERY (A. K. Banga, 1998) is herein incorporated as reference in regards to enhancement of polar neutral, molecule delivery by current-induced electroosmosis. It is clear that the composition of the cream or gel is critical for improvement in transport when lipophilic drugs such as Cetylated fatty esters are used with iontophoretic methodologies.

For this disclosure, "transdermal" drug delivery is meant to be the administration of a drug to the skin surface of an individual so that the drug passes through the skin tissue and into the individual's tissue or blood stream. The term "topical administration" is used in its conventional sense to mean delivery of an active agent to a body surface, such as the skin or mucosa, as in, for example, topical drug administration in the prevention or treatment of various skin disorders, arthritic conditions and musculocutaneous ailments, and the like. "Diffusion" is the movement of molecules through a domain, by random molecular movement, from high concentrations to low concentration. "Flux ($J_{ss}$)" is the amount of permeant crossing the skin or entering systemic circulation. This is measured as mass/area/time (or mg cm$^{-2}$ hr$^{-1}$). "Permeant" is selectively defined for this disclosure as the molecular species of disclosed interest that moves through or is moving into the skin or tissue. "The molecular species of disclosed interest" in this disclosure are the Cetylated fatty esters.

BRIEF SUMMARY OF INVENTION

One of the objectives of the present invention is to provide a system by which specific medicinal agents, the molecular species of disclosed interest, can be more efficiently delivered through topical applications into the body. While several formulation enhancements have been described previously, the utilization of phonophoresis and iontophoresis to enhance transdermal delivery of this group of molecules has not been described. The need for such mechanical enhancements may not be readily apparent because the Cetylated fatty esters are highly lipophilic, and this is a favorable characteristic for transdermal delivery. A wide variety of long-chain fatty acids, for example, increase transdermal delivery; the most popular is oleic acid. Aungst et al., Int. J. Pharmaceut., 33, pp. 225-234 describes the utilization of fatty acids and fatty alcohols to enhance transdermal penetration of Naloxone. Unsaturated fatty acids and alcohols were more effective than saturated ones. It is logical that the Cetylated fatty acids also share some of these characteristics.

Further, the anti-inflammatory properties of these Cetylated molecules have been demonstrated through successful transdermal applications for a number of inflammatory conditions. Even our own studies [Sharan et al., Manual Therapy, 14 (supp), pp. S1-53 (2009)] suggest that effective levels of Cetylated fatty ester delivery could be demonstrated through topical cream applications. The need for further enhancement in delivery may not necessarily be apparent, given the successful clinical utilization of the topical treatments, but, given the possible enhancements of phonophoresis seen clinically with other medicinal agents, the use of ultrasound was investigated as a possible source of greater enhancement. Some but not all molecules with similar mass or greater have been shown to be given greatly enhanced transdermal deliveries through the use of phonophoresis. Further consideration was that barrier functions of the skin restrict systemic delivery concentrations compared to oral delivery. Therefore, we developed formulations specifically for use with phonophoresis and iontophoresis.

In summary of these points, the presence of the cetyl chain greatly increases the lipophilic characteristics, due to the alkane cetyl chain. As we have disclosed previously in U.S. patent application Ser. No. 12/608,963, Barathur and Bookout, submitted Oct. 29, 2009, the use of Cetylated fatty esters in combinations with chemical penetrants in topical delivery formulations greatly improves delivery of these Cetylated molecules and even to utilize them also with these formulations as penetration facilitators for other molecules. It was on the basis of these disclosures that further research was performed by us in order to find additional means of enhancing transdermal flux. The results from these studies helped us develop the disclosed invention of using specific formulations either in the form of a gel or a cream using phonophoresis or iontophoresis.

One aspect of the present invention involves innovations whereby topical formulations for the delivery of medicinal Cetylated fatty esters can be combined with to enhance the drug flux through the stratum corneum and into the deeper layers of the underlying tissues. This is achieved through the effective use of Cetylated fatty esters with chemical enhancer combinations in topical formulations with ultrasound. The ultrasound utilization is optimized in regards to modulated frequencies, amplitudes or phases or all three parameters. In this way the lag time associated with passive diffusion of the Cetylated fatty esters is reduced by utilizing the ultrasound energy to increase skin permeability and to provide improved flux through diffusion pathways.

In a further aspect of this invention, topical formulations were developed and modified to enhance delivery of medicinal Cetylated fatty esters when combined with iontophoresis or sequential combinations of both iontophoresis and phonophoresis as an improved delivery system. The use of electrical current in this embodiment works in conjunction with electrolytes and additional penetrant enhancers in the coupling media to open molecular pathways for diffusion as well as hydration of the stratum corneum, allowing for the mass transport of solvent contents in the process. Iontophoretic conditions have been optimized in regards to electrolyte composition, pH and current parameters.

Still further aspects of this invention, are the formulations that provide improved delivery through the skin of the Cetylated fatty esters, while incorporating molecular enhancements that improve the efficiency of both ultra-sound and iontophoretic techniques. The composition of the final formulations can be either that of a cream or a gel. The chemical permeation enhancers are unique in their functional characteristics. While other systems may be available for enhancement, the present combination for use with Cetylated fatty esters, in conjunction with phonophoresis and iontophoresis, has not been described, to our knowledge. It was not clear at the time of these discoveries, if the use of these mechanical methods of enhancement would provide improvement, as many reports have shown no improvement with some pharmaceutical drugs when these methods were used [for example, Williams, Ultrasonics, 28, pp. 137-141 (1990) is Incorporated herein as reference].

As examples of the driving forces utilized in this disclosure, these include but are not limited to: acoustic energy through use of ultrasound; iontophoresis, electroporation, and electro-osmosis; heat where increase in temperature is utilized to enhance transport of Cetylated fatty esters; and pressure gradients where the apparatus used has capacity to provide either a positive or negative pressure gradient across the area of application and this mechanical enhancement is used.

In a further aspect of this invention, this combination of Cetylated fatty esters and chemical enhancement with phonophoresis or iontophoresis for delivery is novel for use in treatment applications of various inflammatory conditions, such as osteoarthritis, rheumatoid arthritis, musculocutaneous injuries, tendinitis, Achilles tendinitis, tenosynovitis, bursitis, chronic patellar tendinitis, epicondylitis, periarticular soft tissue swelling, fibrositis, inflammation of spine, discogenic lower back pain, repetitive strain injuries, myofascial pain syndrome, fibromyalgia, polymyalagia rheumatic, peripheral neuropathies, herpetic neuropathies and Sjogren's syndrome. These applications are novel in that the present invention provides a new approach for increasing the effectiveness of treating these disorders.

The foregoing objects and advantages of the invention are illustrative of those that can be achieved by the present invention and are not intended to be exhaustive or limiting of the possible advantages which can be realized. Thus, these and other objects and advantages of the invention will be apparent from the description herein or can be learned from practicing the invention, both as embodied herein or as modified in view of any variation which may be apparent to those skilled in the art. Accordingly, the present invention resides in the novel, formulation compositions and utilization of mechanical enhancement systems as herein described.

BRIEF DESCRIPTION OF THE DRAWING

FIG. 1 shows treatment responses for the period from the initial visit (w0) though the 4$^{th}$ week (w4). Scoring, as indicated by NPD-VAS Avg Score, was done using the neck pain and disability visual analogue scale for data acquisition. Participants receiving only topical Cetylated fatty acid cream applications are denoted in the figure responses as ( Cet FA alone). Those participants receiving topical Cetylated fatty acid cream plus therapeutic augmentation are denoted in the figure responses as ( Cet FA+TherAug). The significance of these findings in relation to this application are noted in Example 2, paragraph [059].

DETAILED DESCRIPTION OF THE INVENTION

The present invention provides a means of enhancing the rate of permeation of the Cetylated fatty esters through the skin by means of combining an enhancement media with ultrasound therapy. This invention also provides similar enhancement through the combined use with iontophoresis instead of ultrasound. The coupling media, in which the medicament Cetylated fatty esters are applied to the skin, is formulated in such a way as to promote transdermal delivery as well as to improve sound or electrical conductance, and maximizing energy transmission to the skin and deeper inner tissues.

The Disclosed Formulation

The Cetylated fatty esters for this disclosure have been defined as a select group of fatty acids that have been converted synthetically into cetyl esters, some with saturated and some unsaturated hydrocarbon chains, but with the number of carbon atoms of these chains ranging from 10 to 18 or more in length. The composition of these select groupings often includes but is not limited to the inclusion of cetyl oleate, cetyl palmitoleate and cetyl myristoleate. Other fatty acids, which can be cetylated and utilized in the select groups, may be saturated, mono- to poly-unsaturated, or may contain functional groups such as methoxy-, amino- or ring structures. The preferred formulations contain a concentration of 4-40% cetylated fatty esters. Most preferred concentrations being 5-10%. The concentration of individual cetylated fatty acids within typically ranges from 1-60% of the select group, depending on the cetylated molecule. Also, depending on the condition being treated 3-12 cetylated fatty ester molecular forms may comprise the select group.

The formulations of said coupling vehicle have compositions that include polar emulsifiers, cream base, ionic salts, preservatives, antioxidants, fragrance and water. The coupling vehicle may also include other chemical penetrant molecules.

Preferably, the polar solvent/emulsifier material in this invention is propylene glycol. The polar solvent provides hygroscopic and miscible properties that allow solubility for the cetylated esters. This miscible form of Cetylated fatty acids is used as a penetrating agent and once introduced the cetylated fatty esters by themselves serve as medicaments in treatment of various types of pain described previously in this disclosure. A property of propylene glycol, critical for this disclosure, is its ability to hydrate the skin, bringing the flux of water molecules into the stratum corneum. Other polar solvents used instead of or in conjunction with propylene glycol include glycerol, ethylene glycol, 1,2,6-hexane triol, 1,2,4-butane triol, propylene glycol ether of methyl glucose or sorbitol, PEG 40 hydrogenated caster oil, dimethicone copolyol, and polyethylene glycol (preferably, PEG 50, PEG 100 and PEG 500). One or more polar solvents may be used in combination in a final combined concentration of 5-30%.

The incorporation of menthol is disclosed for this invention as a preferred component. The concentration preferred is 1-5%. Its inclusion provides vasodilatation properties that work in conjunction with either phonophoretic or iontophoretic enhancement to increase delivery of the cetylayed fatty esters and this vasodilator which has medicinal properties of its own. Vasodilatation of the capillaries directly beneath the basal layer shortens systemic delivery time and increases concentrations delivered in a shorter period of time. Menthol is also transdermally delivered in higher concentrations through use of phonophoresis or iontophoresis. Another preferred component is eucalyptus oil (1-5%) which, like menthol, adds analgesic effects to the medicinal effects of the Cetylated fatty esters. Other envisioned and preferred embodiments include ubiquinone, an inosine monophosphate dehydrogenase inhibitor, methyl salicylate, lavender oil, capsaicin and camphor, together or separately.

Examples of antioxidants suitable for disclosed formulations include tocopherols, ascorbic acid and its esters, alpha lipoic acid, thiourea, and chelating agents like EDTA and citric acid.

Preferably, the pH of the formulations range from 4.0 to 8.0. The range of ph 4.0 to 6.8 is more preferable, but the most preferred range is pH 5.0 to 6.6. For utilization in the iontophoretic applications the ionic strength is modified to optimize conductance. Compounds useful as pH regulators include, but are not limited to sodium citrate, sodium acrylate, phosphate buffers, sodium or potassium hydroxide, glycerol buffers and triethanolamine. Sodium chloride or potassium chloride are preferred regulators for adjustment in conductance as needed.

The thickening agents composing the formulation base include but are not limited to carbomer polymers (Carbopol 940 NF, Carbopol 934 NF, Carbopol Aqua CC,), hydroxycellulose, polyvinylacetate, polybutylacrylate, PEG 100 stearate, polymethylacrylate, polydimethylsiloxane, hydrogels (e.g., high molecular weight polyvinylpyrrolidone, oligomeric polyethylene oxide, or a mixture thereof) and organogels. PEG 40 hydrogenated caster oil or polyethoxylated castor oil may be used for proper composition in conjunction with the thickening agents. Other suitable components such as alcohol may be included up to 10%. Preferred alcohols are ethanol, 2-propanol and methanol. Water is preferably present at concentrations up to 80%. There are two preferred viscosities for application: Low (40-50 Kcps) for cream and gel and Medium (70-80 Kcps) for gel.

Example of preservatives include, but are not limited to benzalkonium chloride, cetrimide, benzethonium chloride, imidizolidinyl urea, benzyl alcohol, isopropyl alcohol, triclosan, hydantoin derivatives, phenyoxyethol, imidazolidinylurea and parabens. Preferably the preservative is methyl paraben, propyl paraben, or a mixture thereof.

For phonophoretic application, a cream, gel or lotion is a preferred type of coupling media formulation. For iontophoretic application, a gel is a preferred type of coupling media formulation. For use with drug electrodes having a delivery matrix pad, the formulation without thickening agents is preferred. However, these preferences do not restrict the type of agent for each application.

Phonophoresis

"Ultrasound" is ultrasonic radiation of a frequency above 20,000 Hz. The present invention employs frequencies in the range of about 20-2,500 kHz, preferably in the range of 500-1,500 kHz. Preferred intensity is less than 5.0 W cm$^{-2}$ and especially preferred at 0.01 to 5 W cm$^{-2}$. With continuous beam intensity the preferred range is 0.5-2.5 W cm$^{-2}$. The use of continuous ultrasound provides thermal heating, which is further conducive for enhanced delivery of Cetylated fatty esters. It is also the continuous mode that is preferred when utilized with conditions, in which movement is restricted. Use of discontinuous pulsing reduces heating effects when needed while still facilitating diffusion through the other properties of ultrasound application, which are thought to include oscillating of particles in the tissue and in the drug delivery composition, decreasing of membrane potential and increased cell permeability, increasing ion conductance and alterations in the skin-lipid structure. Discontinuous pulsing may be preferred for acute pain and inflammation. For these conditions a preferred pulsing cycle is 1 MHz frequency with 3 pulse/cycle using a 3.3 msec pulse during, 10 msec periods.

It is emphasized that these ranges are intended to be merely illustrative of preferred embodiment; in some cases, higher or lower frequencies may be used. Ultrasound may be pulsed or continuous, but preferably continuous when used at lower frequencies. For continuous mode ultrasound, the preferred frequency is 1 MHz with an intensity of 1.0 W·cm$^{-2}$. At high frequencies, pulsed application is generally preferred to enable generated heat dissipation.

The duration of ultrasound treatment may vary with the condition and severity, preferably 5-45 min in either continuous or pulse mode, more preferably 5-30 min, most preferred 5-10 minutes. Preferred phonophoresis treatment frequency recommended for this invention is 3-4 times per week for 3 weeks. This may be repeated as needed.

Prior treatment before ultrasound or with simultaneous application of drug in coupling media with ultrasound is envisioned as effective approaches in this invention. It is, therefore, effective when the affected area on the individual is first treated with ultrasound, providing the effects of ultrasound directly to that area, then followed by application of the coupling vehicle containing Cetylated fatty esters and allowing for enhanced delivery and further treatment through the reapplication of ultrasound.

"An ultrasound device" includes one or more ultrasound devices necessary to carry out the present invention and "administration methods" denote one or more methods currently known or become known after the reading of this disclosure.

Iontophoresis

The present invention in another embodiment accomplishes trandermal enhancement through the use of current applied through the vehicle coupling media in intensities equal to or less than 0.5 mA cm$^{-2}$. The preferred range is 0.2-0.5 mA cm$^{-2}$. The preferred electrode for drug delivery is positive; however, the use of drug delivery using the negative electrode may also be possible due to the somewhat neutral properties of the Cetylated fatty esters. Current levels may range from 0.5 to 5 mA depending on electrode area size. Drug electrodes with delivery capacity of 1 to 3 cc are preferred depending on the size of area affected on the individual and the severity. Maximum preferred dosage is 40 to 80 mA-minutes. The use of iontophoretic devices with ramp up and ramp down capacity is preferred to provide 30 second ramping at 0.006 to 0.01 mA cm$^{-2}$.

In an extension of this embodiment, when iontophoresis is used to enhance delivery of the permeant of interest, the subsequent application of ultrasound to the same applied area further increases the effects of the delivery.

"An iontophoresis device" includes one or more iontophoretic devices necessary to carry out the present invention and "administration methods" denote one or more methods currently known or become known after the reading of this disclosure.

Example 1

The following are representative of compositions which can be formulated within the scope of this invention. They are for illustrative purpose only and are not intended to define the scope of the invention. Formulations are prepared through combining components with compatible mixing properties at elevated temperatures and then mixing components together while lowering the temperature, followed by adding those components with greater thermolability. All compositions are presented by % weight per volume.

Cetylated fatty esters cream formulation contained several cetylated fatty esters and 1.5% w/w menthol in a cream base (with cream composition based on Formula C in Example 1, having a pH of 6.5). Placebo cream had the same composition but without cetylated fatty esters.

Data was collected through the following sources: therapist work up, tenderness to palpation, algometer readings and for each trigger point, Cervical Range of Motion measurements (CROM●), and written participant responses to three evaluators, namely: a) neck pain and disability visual analogue scale (NPDVAS), b) Neck Disability Index (NDI), and c) the 36-item short-form health survey (SF36).

Physical augmentation plus the topical cetylated fatty esters applications provided the fastest and most effective treatment modality of the study. Efficacy results allowed for the following rankings—a) for pain (NPDVAS and SF36 pain index): cetylated fatty esters topical plus physical augmentation was more effective that cetylated fatty esters topical alone; b) for neck disability (NDI): cetylated fatty esters topical plus physical augmentation was more effective that cetylated fatty esters topical alone; c) for life quality (SF36 total index): cetylated fatty esters topical plus physical augmentation was more effective that cetylated fatty esters topical alone; d) for SF36 (physical activity index): Cetylated fatty esters topical plus physical augmentation was more effective that cetylated fatty esters topical alone; e) for range of motion (CROM): Cetylated fatty esters topical plus physi-

| COMPONENT | FORMULATION A | FORMULATION B | FORMULATION C | FORMULATION D |
|---|---|---|---|---|
| Cetylated Fatty Esters | 5-10% | 15-20% | 5-10% | 5-10% |
| Menthol | 1-5% | 1-5% | 1-5% | 1-5% |
| *Eucalyptus* Oil | 1% | — | 1% | — |
| Polar Solvents | 12% | 15% | 8% | 10% |
| Disodium EDTA | 0.1% | 0.1% | 0.1% | 0.1% |
| Carbomer 940 NF | 0.7% | 0.2% | 0.5% | — |
| PEG 100 Stearate | — | — | — | 0.5% |
| Hydroxycellulose | — | — | — | 1% |
| Anti-oxidant | 0.5-2% | 0.5-2% | 0.5-2% | 0.5-2% |
| Cremophore RH 40 | 1% | — | 0.5% | — |
| Fragrance | 0.02-1% | — | 0.02-1% | — |
| Purified Water | q.s. | q.s. | q.s. | q.s. |
| Preservative | 0.1-0.2.2% | 0.1-0.2.2% | 0.1-0.2.2% | 0.1-0.2.2% |
| Sodium Hydroxide | To pH 5.5 | To pH 5.0 | To pH 6.5 | — |
| Triethanolamine | — | — | — | To pH 5.8 |
| Electrolyte Salts | As needed for optimal conductance | As needed for optimal conductance | As needed for optimal conductance | As needed for optimal conductance |
| Use Indicated with Phonophoresis | X | X | X | |
| Use Indicated with Iontophoresis | X | X | X | X |

Example 2

An assessment was made in order to measure what enhancements could be derived from combining topical delivery of Cetylated fatty esters with physical therapeutic enhancing systems. Patients with myofascial pain syndrome of the neck and shoulders, with at least 2 trigger points (MTrPs), were randomized into 2 groups: a) topical Cetylated fatty esters cream application only (n=35), and b) topical Cetylated fatty esters cream application plus physical augmentation (n=37). Therapeutic sessions providing physical augmentation were given twice per week if designated and topical cream was applied liberally twice daily if designated. This baseline comparison study followed patients for 4 weeks with 3 assessment visits.

cal augmentation was again more effective than cetylated fatty esters topical alone. Topical administration of cetylated fatty esters resulted in a significant reduction in pain and neck disability by the end of the 4 week period. However, cetylated fatty esters topical therapy was significantly improved when combined with therapeutic augmentation.

When combined with physical augmentation, improvements of patient conditions were better in most measurements than physical augmentation with a placebo cream application.

Example 3

Results from therapeutic augmentation led to evaluation of using ultrasound to augment topical cetylated fatty esters delivery. A gel base similar to that in example 1 (formulation C), containing 5-10% cetylated fatty esters was used in treatments of: myofascial pain syndrome, fibromyalgia, tennis elbow, wrist tendinitis, supraspinatus tendinitis, low back pain, knee osteoarthritis, sprains, joint inflammation after post operative joint stiffness, and golfer's elbow (n=40) with ultrasound delivery augmentation (1 MHz at 1.0 W cm$^{-2}$, with treatment duration of 7 minutes). Probe position through the gel allowed for a 0.2 and 1.5 mm distance from the skin. The rise in temperature at the application site during the 7 minute period of continuous ultrasound averaged about 3° C. Decreases in treatment response time and improvements in degree of response were noted compared to topical cetylated fatty esters treatment alone. While in the previous example, the average response time for significant improvements in pain reduction took approximately 2 weeks (cetylated fatty esters plus therapeutic augmentation), the average response time with phonophoretic augmentation of topical cetylated fatty esters delivery was reduced to 4-7 days.

Example 4

A group of 11 patients with osteoarthritis of lower back or knee were treated with phonophoresis (1 MHz at 1.5 W cm$^{-2}$, with treatment sequence duration of 10 minutes continuous pulse, followed by 3 minutes of no pulse, followed by another 10 minutes of continuous pulse) with application of the cetylated fatty esters in the coupling media (a formulation like the of Formulation A in Example 1) to the general area over the affected joint(s). With daily treatment, most noted significant improvements within 3-10 days. These results were much sooner than expected.

Example 5

The cream version (a Formulation A of Example 1) of this invention has been clinically tested further with phonophoresis with an ultrasound machines at 1 mZh (1 W cm$^{-2}$; continuous, with duration 7 minutes per treatment) in several hundred patients in clinical settings. Patient conditions included knee pain from Osteoarthritis, discogenic back pain, tendinitis, bursitis, fibromyalgia, carpal tunnel syndrome and other pain disorders. The vast majority of these patients noted significant improvements in pain within 3-7 days. Similarly, a gel version of this invention (formula A of Example 1) has been clinically tested with an ultrasound machine set at 1 mHz (1-2 W cm$^{-2}$; continuous, with durations ranging from 5-10 minutes per treatment) a number of patients. Patient conditions included knee pain from osteoarthritis, discogenic back pain, tendinitis, bursitis, fibromyalgia, carpal tunnel syndrome, repetitive strain injuries and other pain disorders. Further, a lotion version of this invention (formula B of Example 1) is proposed to be used with ultrasound set at 1 mHz. Patient conditions will include knee pain from osteoarthritis, back pain, tendinitis, bursitis, fibromyalgia, carpal tunnel syndrome, repetitive strain injuries and other pain disorders. While different responses were noted with the different conditions, severity and individuals, all responses were favorable, similar to other examples given herein.

Example 6

Formulations for effective use with iontophoresis have been developed. Those with best efficacy are indicated in Example 1, formulations B and D. Iontophoretic settings chosen was 4 mA for total delivery of 20 mA-min and applying cream using the positive electrode. This combination is given as an example and does not limit the use of other treatment combinations.

Modifications and variations of the present invention will be obvious to those skilled in the art from the foregoing detailed description, and are intended to come within the scope of the appended claims.

REFERENCES CITED

| U.S. PATENT DOCUMENTS | | | |
|---|---|---|---|
| 3,934,013 | January 1976 | Poulsen | 424/239 |
| 3,989,816 | November 1976 | Rhaadhyaksha | 424/60 |
| 4,017,641 | April 1977 | DiGiulio | 424/365 |
| 4,049,824 | September 1997 | Diehl | 424/312 |
| 4,113,881 | September 1978 | Diehl | 424/312 |
| 4,343,709 | August 1982 | Fawzi | 210/782 |
| 4,537,776 | August 1985 | Cooper | 514/424 |
| 4,864,970 | September 1989 | Patel and Chang | 122/32 |
| 5,026,556 | June 1991 | Drust et al | 424/449 |
| 5,115,805 | May 1993 | Bommannan et al. | 128/24 |
| 5,569,675 | October 1996 | Diehl | 514/549 |
| 5,947,921 | September 1999 | Johnson et al. | 604/22 |
| 6,417,227 | July 2002 | Lord and Lytle | 514/529 |
| 6,677,321 | January 2004 | Levin | 438/612 |
| 7,612,111 | November 2009 | Spencer and Millsap | 514/557 |
| 7,772,279 | August 2010 | Leonard and Simonton | 514/549 |
| 7,776,914 | August 2010 | Spencer and Millsap | 514/557 |
| US Patent Application | | | |
| 12,608,963 | October 2009 | Barathur and Bookout | |
| FOREIGN PATENT DOCUMENTS | | | |
| 43,738 | January 1982 | Wickett et al. | Europ. Pat. Office |

OTHER REFERENCES

Aungst et al., Int. J. Pharmaceut., 33, pp. 225-234

Bhatia et al., "Effect of penetration enhances and iontphoresis on the FT-IR spectroscopy and LHRH permeability through porcine skin," Journal of Controlled Release, 47, pp. 81-89 (1997)

Brown et al., "Chapter 5. Transdermal drug delivery systems: skin perturbation devices," Meth. Molec. Biol., 437, pp. 119-139 (2008)

Choi et al., Appl. Skin Physiol., 12, pp. 326-335 (1999);

Clancy et al., "A comparison of the effects of electric current and penetration enhancers on the properties of human skin using spectroscopic (FT-IR) and calorimetric (DSC) methods," International Journal of Pharmaceutics, 105, pp. 47-56 (1994)

Edwards, CMO (cerasomol-cis-9-cetyl myristoleate) in the treatment of fibromyalgia: an open pilot study," J Nutr Environ Med, pp. 105-111 (2007);

ELECTRICALLY ASSISTED TRANSDERMAL AND TOPICAL DRUG DELIVERY (A. K. Banga, 1998)

Gangarosa et al. Journal of Pharmacology and Experimental Therapeutics, 212, pp. 377-381 (1980)

Ghosh, T. K. et al., Pharmaceutical Technology, 17, p. 62 (1993);

Ghosh, T. K. et al. Pharmaceutical Technology, 17, p. 68 (1993);

Ghosh, T. K. et al. Pharmaceutical Technology, 17, p. 72 (1993).

Hesslink et al., "Cetylated fatty acids improve knee function in patients with osteoarthritis," J Rheumatol, 29, pp. 1708-1812 (2002);

Hunter et al., "Synthesis of cetyl myristoleate and evaluation of its therapeutic efficacy in a murine model of collagen-induced arthritis," Pharm Res, 47, pp. 43-47 (2003).

Kraemer et al., "Effect of a Cetylated fatty acid topical cream on functional mobility and quality of life of patients with osteoarthritis," J Rheumatol, 31, pp. 767-774 (2004);

Kraemer et al., "Fatty acid topical cream with menthol reduces pain and improves functional performance in individuals with osteoarthritis," J Strength Condit Res 19, pp. 475-480 (2005)

Kraemer et al., "Effects of treatment with a Cetylated fatty acid topical cream on static postural stability and plantar pressure distribution in patients with knee osteoarthritis," J Strength Condit Res 19, pp. 115-121 (2005)

Mitragotri, Pharm. Research, 17, pp. 1354-1359 (2000)

Le et al., Pharm. Res., 17, 1151-1154 (2000)

PERCUTANEOUS PENETRATION ENHANCERS (Eric W. Smith & Howard I. Maibach eds. 1995);

Sharan et al., "The effect of Cetylated fatty esters and physical therapy on myofascial pain syndrome of the neck. Manual Therapy, 14 (supp), pp. S1-53 (2009);

Siemandi, "The effect of cis-9-myristoleate (CMO) and adjunctive therapy on arthritis and autoimmune disease—a randomized trial," Townsend Lett Doctors & Patients, August/September, pp 58-63 (1997);

Williams, Ultrasonics, 28, pp. 137-141 (1990)

What is claimed is:

1. A method of enhancing the rate of permeation of cetylated fatty esters through the skin comprising steps:
   a. Topically applying to a portion of skin a composition comprising:
      i. four or more cetylated fatty acid esters, said cetylated esters are present in amounts ranging from 4-40%, and are selected from the group consisting of cetyl oleate, cetyl palmitate, cetyl myristoleate and those having saturated or unsaturated hydrocarbon chains having 10 or more carbon atoms; and
      ii. one or more polar solvents present in amounts ranging from 5-30%, wherein the solvents are selected from the group consisting of 1,2,4-butane triol, dimethicone copolyol, ethylene glycol, glycerol, glyceryl monostearate, 1,2,6-hexane triol, propylene glycol ether of methyl glucose or sorbitol, PEG 40 hydrogenated caster oil, polyethylene glycol and propylene glycol; and
   b. Applying phonophoresis or iontophoresis to the same portion of skin; wherein step b can optionally be performed before step a.

2. The method according to claim 1, wherein the one or more polar solvents comprises a polyethylene glycol selected from the group consisting of PEG 50, PEG 100 and PEG 500.

3. The method according to claim 1, wherein the composition is in the form of a gel, lotion, foam, spray or cream.

4. The method according to claim 1, wherein the composition further comprises menthol in amounts ranging from 1-20%.

5. The method according to claim 1, wherein the composition has a pH ranging from 4.0 to 8.0.

6. The method according to claim 1, wherein the phonophoresis utilizes ultrasound, with continuous or discontinuous pulsing, in the range of 20 to 2,500 kHz to enhance the delivery of the cetylated fatty acid ester of claim 1.

7. The method according to claim 1, wherein the phonophoresis utilizes a beam intensity of less than 5.0 W cm$^{-2}$.

8. The method according to claims 1, where the penetration of the cetylated fatty acid ester though the skin is enhanced by 200% or more, when the phonophoresis utilizes ultrasound, with continuous or discontinuous pulsing, in the range of 20 to 2,500 kHz, and has a beam intensity of less than 5.0 W cm$^{-2}$.

9. The method according to claim 1, wherein the ionophoresis generates a low level electric current, with a current intensity ranging from 0.5 to 20 mA, which facilitates the transdermal flux of the cetylated fatty acid esters.

10. A method of treating inflammatory conditions, comprising the steps of
   a. Topically applying to a portion of skin a composition comprising:
      i. four or more cetylated fatty acid esters, said cetylated esters are present in amounts ranging from 4-40%, and are selected from the group consisting of cetyl oleate, cetyl palmitate, cetyl myristoleate and those having saturated or unsaturated hydrocarbon chains having 10 or more carbon atoms; and
      ii. one or more polar solvents present in amounts ranging from 5-30%, wherein the solvents are selected from the group consisting of 1,2,4-butane triol, dimethicone copolyol, ethylene glycol, glycerol, glyceryl monostearate, 1,2,6-hexane triol, propylene glycol ether of methyl glucose or sorbitol, PEG 40 hydrogenated caster oil, polyethylene glycol and propylene glycol; and
   b. Applying phonophoresis or ionophoresis to the same portion of skin; where step b can optionally be performed before step a;

wherein the inflammatory condition is selected from the group consisting of osteoarthritis, rheumatoid arthritis, inflammation of the spine, discogenic back pain, polymyalagia pheumatic, musculocutaneous injuries, tendinitis, Achilles tendinitis, tenosynovitis, bursitis, chronic patellar tendinitis, epicondylitis, periarticular soft tissue swelling, repetitive strain injuries, myofascial pain syndrome, fibrositis, fibromyalgia, peripheral neuropathies, herpetic neuropathy and Sjogren's syndrome.

* * * * *